United States Patent [19]

Scott et al.

[11] 4,089,224
[45] May 16, 1978

[54] ACOUSTIC EMISSION FATIGUE ANALYZER

[75] Inventors: William R. Scott, Andalusia; John M. Carlyle, Willow Grove, both of Pa.

[73] Assignee: The United States of America as represented by the Secretary of the Navy, Washington, D.C.

[21] Appl. No.: 772,040

[22] Filed: Feb. 25, 1977

[51] Int. Cl.² ............................................. G01N 3/00
[52] U.S. Cl. ...................................... 73/587; 73/88 R
[58] Field of Search ............... 73/67, 67.3, 71.4, 88 R, 73/100, 91, 587, 577, 578

[56] References Cited

U.S. PATENT DOCUMENTS 3,782,183  1/1974  O'Connor et al. ...................... 73/100

OTHER PUBLICATIONS

Y. Nakamura, Acoustic Emission Monitoring System for Detection of Cracks in a Complex Structure, Materials Evaluation, Jan. 1971, pp. 8–12, 73–88.3.

Primary Examiner—Richard C. Queisser
Assistant Examiner—John P. Beauchamp
Attorney, Agent, or Firm—R. S. Sciascia; Henry Hansen

[57] ABSTRACT

A device for acquiring and displaying acoustic emission fatigue data so as to facilitate the interpretation of dynamic micromechanical failure processes in materials. The load on a specimen under cyclic loading is monitored by a load cell whose output is sent to a cycle counter. The specimen is also monitored by a transducer which senses acoustic emissions. The signal produced by the transducer passes through a preamplifier, filter, amplifier and threshold detector to a pulse generator whose output is connected to the intensity modulation input of an oscilloscope or other cartesian coordinate arraying device. The load cell output is also connected to the vertical deflection input of the oscilloscope. The counter output is connected to the horizontal deflection input of the oscilloscope. Every time that the transducer detects an acoustic emission event, that event is represented on the oscilloscope in a two-dimensional cartesian coordinate system as a dot whose ordinate corresponds to the instantaneous load (derived from the load cell) and whose abscissa corresponds to the number of elapsed fatigue cycles (derived from the counter) at the time the event occurred, resulting in the simultaneous recording of the relationship between sample load, acoustic emission rate and number of fatigue cycles. By placing a screen splitter on the vertical deflection input to the oscilloscope, separate records of emissions under rising loads and under falling loads are produced.

18 Claims, 4 Drawing Figures

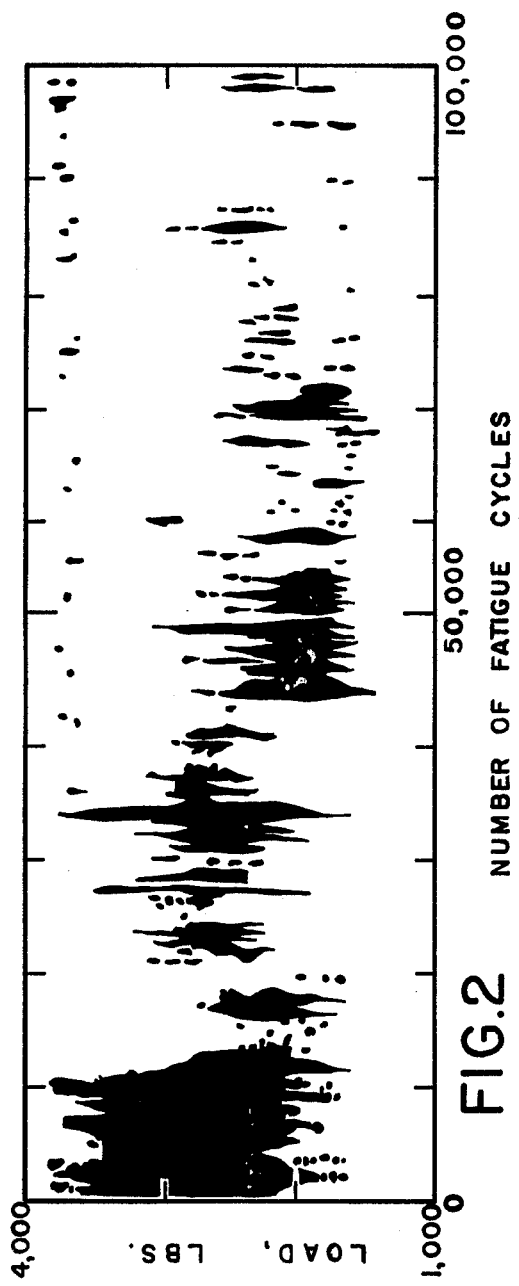
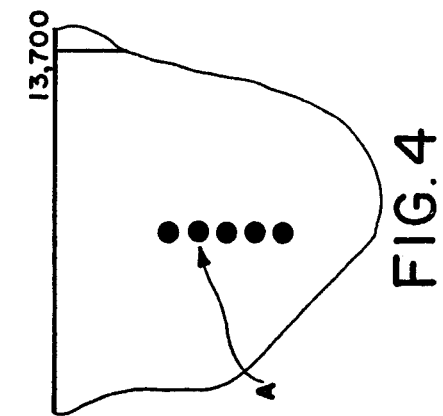
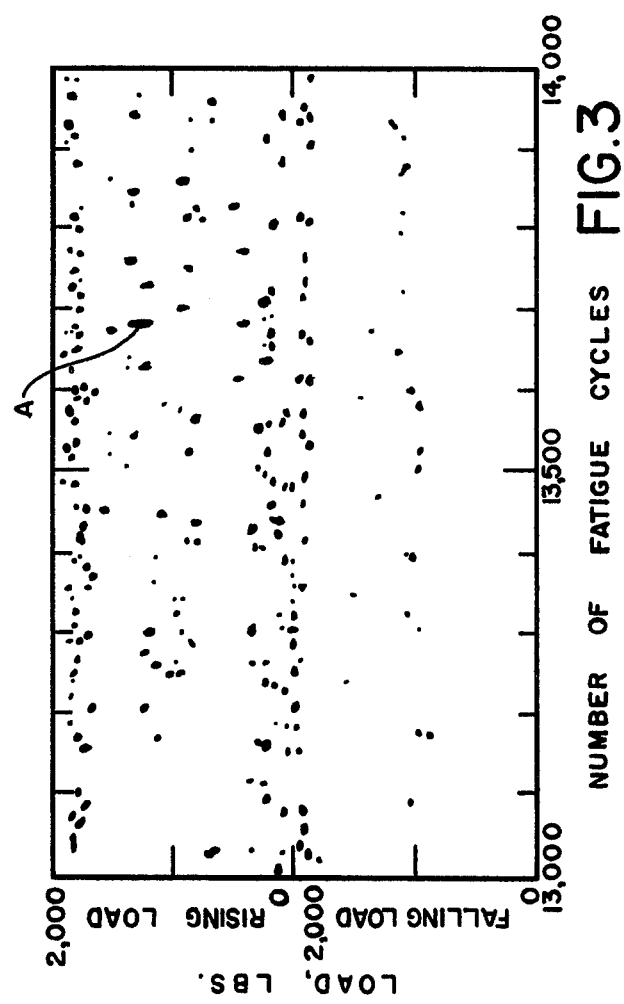
FIG. 2
FIG. 3
FIG. 4

ACOUSTIC EMISSION FATIGUE ANALYZER

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to devices for detecting or measuring degradation of materials or structures, and more particularly to acoustic emission monitoring devices for detecting incipient fatigue damage in materials or structures.

Acoustic emission is a nondestructive testing technique which reacts to the active behavior of defect growth in structures and materials, such as occurs during fatiguing. This technique exploits the fact that any material will tend towards the lowest possible energy state. If a defect such as a microfracture is present in the material, it will have the effect of causing a localized increase in energy, resulting in defect growth when the material reacts to achieve a lower energy state. Coincident with this growth, a stress wave (also referred to as an acoustic emission) will propagate through the material, with the defect being the epicenter of the stress wave. Thus, detection of such a wave indicates that a growing defect is present in the material. Also, since the growing defect itself creates the stress wave, the characteristics of the stress wave are dependent upon the nature of the defect, so that monitoring of acoustic emissions produced by material defects can provide information concerning progressive fatiguing or other cracking, and thus impending failure, of the material. Acoustic emission monitoring is extremely sensitive to small dynamic changes, such as subcritical crack growth, in the state of stress of materials. Unfortunately, this sensitivity means that there is a high probability of obtaining irrelevant information, such as background noise, with desired data. In addition, acoustic emission monitoring devices presently in use produce plots of acoustic emission rate or total acoustic emissions versus number of fatigue cycles. While such plots do show the variation in acoustic emission rate or in total acoustic emissions under progressive fatiguing, further interpretation of such data is highly limited, so that an analysis of microfracture processes in materials using this data would yield limited information.

SUMMARY OF THE INVENTION

Accordingly, it is a general purpose of the present invention to provide an acoustic emission fatigue analyzer which facilitates the interpretation of dynamic failure processes in materials.

Other objects of the present invention are to provide an acoustic emission fatigue analyzer which monitors and receives acoustic emissions from a specimen, which produces acoustic emission data which is related more directly to the actual cause of the emissions, which detects and displays acoustic emission occurrences and features which would not be observed with conventional acoustic emission monitoring, and which can provide data for testing of different crack propagation theories which describe at what part of a loading cycle cracks will propagate.

Further objects of the present invention are to provide an acoustic emission fatigue analyzer which is capable of separating the desired signal from background noise such as extraneous load train and gripping noise, and which is capable of data presentation with the separation of phenomena occurring at different load levels.

Briefly, these and other objects of the invention are accomplished by a device which displays each acoustic emission as a dot, located on a two-dimensional cartesian coordinate system, whose ordinate and abscissa correspond to the load and number of fatigue cycles, respectively, at which the event occurred, resulting in the simultaneous recording of the relationship between sample load, acoustic emission rate and number of fatigue cycles. The instantaneous load on a specimen which is being subjected to cyclic loading by a fatigue testing machine or other drive mechanism is monitored by a load cell. Depending upon the position of a double-throw switch, the output of the load cell either is fed directly to the vertical deflection input of an oscilloscope or other cartesian coordinate recording device, or else passes through a screen splitter which adds a constant voltage to either the rising or the falling load signal produced by the load cell, and thence to the vertical deflection input of the oscilloscope. The signal produced by the load cell is also received by a cycle counter which counts the number of cycles of cyclic loading that the specimen has undergone and provides an analog signal proportional thereto to the horizontal deflection input of the oscilloscope. The specimen is also monitored for acoustic emissions by a transducer whose signal triggers a pulse generator every time the signal amplitude exceeds a predetermined threshold level. The output of the pulse generator is received by the intensity modulation input of the oscilloscope. Every time that the specimen produces an acoustic emission which is detected by the transducer, the pulse generator causes a dot to appear on the oscilloscope screen. The ordinate of the dot corresponds to the instantaneous load (from the load cell) and the abscissa corresponds to the number of elapsed fatigue cycles (derived from the counter) at the time the acoustic emission occurred. This results in the simultaneous recording of the relationship between sample load, acoustic emission rate and number of elapsed fatigue cycles.

Other objects, advantages, and novel features of the invention will become apparent from the following detailed description of the invention when considered in conjunction with the accompanying drawings wherein:

BRIEF DESCRIPTION OF THE DRAWINGS

FIG. 2 shows a display produced by the present invention during testing of a specimen;

FIG. 3 shows a second display produced by the present invention resulting from a second test of a different specimen; and FIG. 4 shows a magnified view of one portion of FIG. 3.

DESCRIPTION OF THE PREFERRED EMBODIMENT

Figure 1:
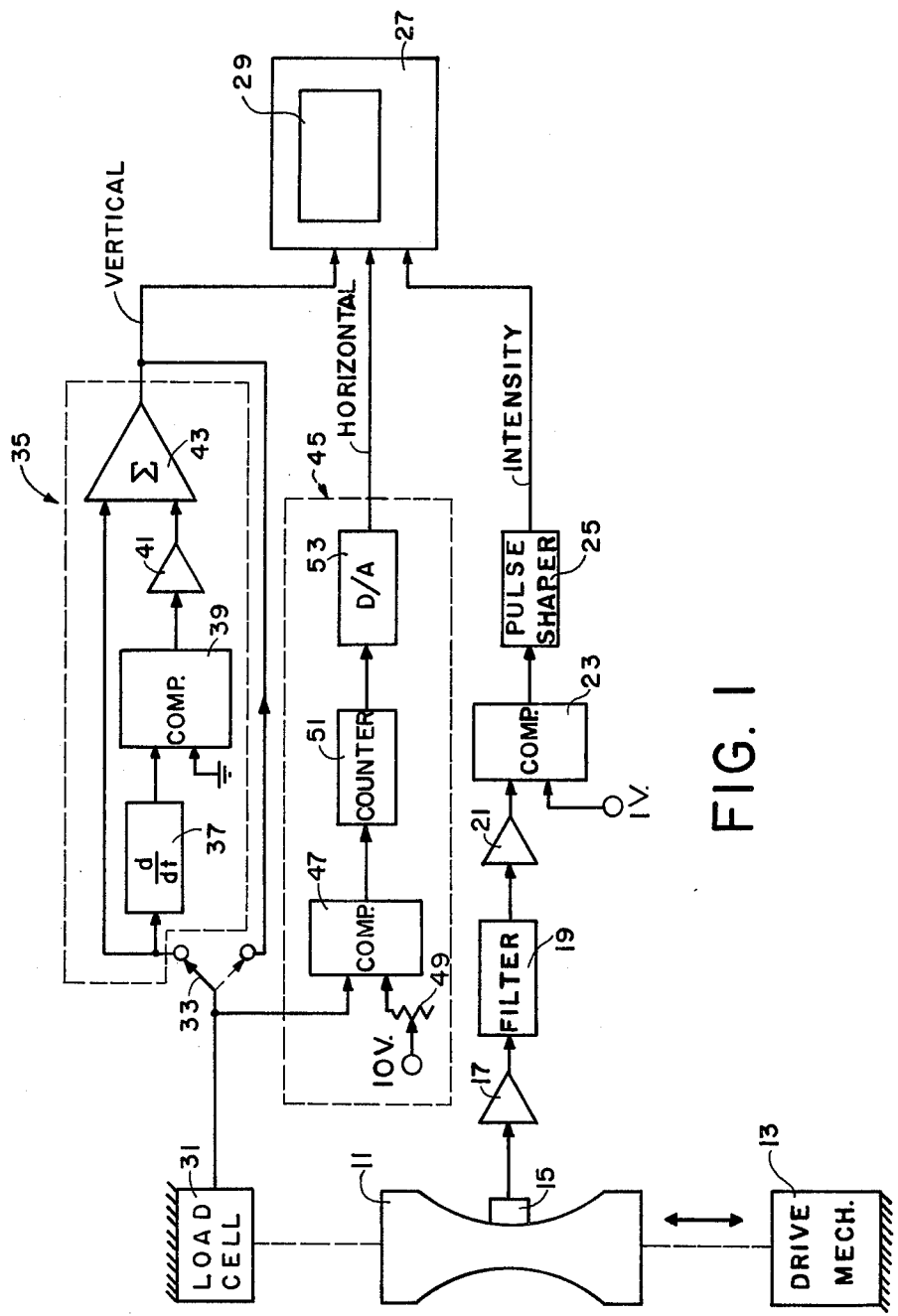
FIG. 1 is a block diagram of an acoustic emission fatigue analyzer according to the present invention.

Referring now to the drawings, there is shown in FIG. 1 an acoustic emission fatigue analyzer, for use in fatigue testing of, and monitoring and analyzing acoustic emissions produced by, a specimen or test sample 11, placed under cyclic stress by driving mechanism 13. The analyzer includes a transducer or acoustic emission sensor 15 which detects acoustic emissions produced by specimen 11. Transducer 15 can be fastened to specimen 11 using glue, rubber band, C-clamp or other fastening means. In addition, any air gap between transducer 15 and specimen 11 should be filled with glycerin, alcohol, oil, water or any other suitable material, so that acoustic emissions are effectively transmitted from specimen 11 to transducer 15. Transducer 15 detects acoustic emissions emanating from growing defects in specimen 11 as it undergoes cyclic stress and is fatigued. Transducer 15 can for example be a 140kHz resonance PZT (lead zirconate titanate) crystal. Electrical signals generated by transducer 15 pass through low noise preamplifier 17 which can for example amplify the signal from the transducer 100 times. The signal produced by preamplifier 17 is filtered by bandpass filter 19 in order to remove extraneous noise due to sources other than acoustic emissions. Filter 19 removes low-frequency noise due to structural vibration and other causes, thus increasing the signal-to-noise ratio, and can have a bandpass centered about the resonance frequency of transducer 15. Filter 19 can for example have a bandpass of 0.1 to 0.3MHz. The signal from filter 19 is then amplified, for example 1000 times, by amplifier 21, whose output is received by comparator 23. Comparator 23 also receives a constant voltage reference signal, which can for example be 1 volt, and produces a positive constant voltage signal for as long as the amplitude of the signal from amplifier 21 exceeds that of the reference voltage (for example, about 10μs duration). The output of comparator 23 is received by pulse shaper or pulse generator 25 which, upon receiving a pulse from comparator 23, produces a pulse of greater duration (for example, about 0.5 ms wide), which signal is received by the intensity modulation input (or Z input) of oscilloscope 27, causing a dot of light to appear on oscilloscope screen 29 whenever an acoustic emission from specimen 11 is detected by transducer 15.

The position of each dot of light which appears on the oscilloscope screen 29 is determined by the instantaneous load and total number of elapsed cycles of cyclic stress (also referred to as fatigue cycles) present when specimen 11 produces the corresponding acoustic emission. These two values are determined using load cell 31 which is connected to, and senses the instantaneous load exerted by drive mechanism 13 on, specimen 11. Load cell 31 produces an electrical signal whose voltage is proportional to the force exerted on specimen 11 by drive mechanism 13. Load cell 31 can for example be a piezoelectric crystal. The signal which load cell 31 generates is provided to double-throw switch 33, with which bypass, or utilization of, screen splitter 35 can be selected. If switch 33 is positioned (as illustrated) so that the signal from load cell 31 passes through and does not bypass screen splitter 35, then the signal from load cell 31 passes through switch 33 and is differentiated by differentiator 37. The differentiated signal is received by comparator 39 whose reference voltage input is grounded (zero volts). Comparator 39 is similar to, and operates in a manner similar to, comparator 23 discussed above. While the differentiated signal is positive, so that the input signal is greater than the reference voltage, indicating that the load applied by drive mechanism 13 to specimen 11 is rising, then comparator 39 produces a constant positive voltage. When the differentiated load cell 31 signal is negative, indicating that the load applied by drive mechanism 13 to specimen 11 is falling, comparator 39 produces a zero voltage signal.

Since drive mechanism 13 is subjecting specimen 11 to cyclic stress, the signal which is produced by comparator 39 is a square wave whose maximum and minimum amplitude are positive and zero voltages respectively and whose frequency is the same as that of the cyclic loading which specimen 11 experiences. The signal from comparator 39 is amplified by amplifier 41. The signals produced by amplifier 41 and by load cell 31 are added by summer 43. Therefore, the signal which is produced by summer 43, and thus by screen splitter 35, is the signal from load cell 31 when the load which is applied by drive mechanism 13 to specimen 11 is falling, and is the signal from load cell 31 plus a positive constant voltage when the load which is applied by drive mechanism 13 to specimen 11 is rising. The output signal from screen splitter 35 is provided to the vertical deflection input (or Y input) of oscilloscope 27 to control the vertical deflections on screen 29 of dots resulting from acoustic emissions detected by transducer 15. Because of the constant voltage which is applied to the load cell 31 signal whenever the load on specimen 11 is rising, a dot on screen 29 resulting from an acoustic emission while specimen 11 is undergoing a rising load of a certain instantaneous magnitude is vertically displaced upwardly from a dot on screen 29 resulting from an acoustic emission while specimen 11 is undergoing a falling load of equal instantaneous magnitude, when screen splitter 35 is used. Thus, screen splitter 35 splits screen 29 horizontally into two displays, the upper display containing those dots resulting from detection of acoustic emissions during rising loads and the lower display containing those dots resulting from detection of acoustic emissions during falling loads on specimen 11. If such separate displays are not desired, then double-throw switch 33 can be positioned so that the signal generated by load cell 31 bypasses screen splitter 35 to go directly to the vertical deflection input of oscilloscope 27.

The output signal of load cell 31 is also received by cycle counter 45 which provides to the horizontal deflection input (or X input) of oscilloscope 27 an analog signal indicating the number of fatigue cycles which specimen 11 has undergone since the beginning of the test being monitored. Cycle counter 45 includes comparator 47, counter 51, and digital-to-analog converter 53. The signal which is generated by load cell 31 is received by comparato 47. Comparator 47 is similar to, and operates in a manner similar to, comparator 23 and comparator 39, discussed above. Comparator 47 also receives a reference voltage signal from potentiometer 49, which receives a constant voltage of, for example, 10 volts. For as long as the amplitude of the load cell 31 signal exceeds the amplitude of the reference voltage signal received by comparator 47, the output signal of comparator 47 is a constant positive voltage. Potentiometer 49 permits variation of the threshold voltage level at which comparator 47 will produce the constant voltage. The amplitude of the reference voltage signal is varied by adjusting potentiometer 49 so that the maximum of the periodic signal produced by load cell 31 exceeds the reference voltage signal, so that comparator 47 produces one output pulse per fatigue cycle experienced by specimen 11. The duration of each pulse is the duration that the amplitude of the signal from load cell 31 exceeds the reference voltage. Counter 51 receives the output signal from comparator 47, and counts and totalizes the number of pulses which comparator 47 produces during a test of specimen 11, which number corresponds to the number of fatigue cycles which specimen 11 experiences. Counter 51 produces a digital signal containing the number of fatigue cycles experienced by specimen 11. The digital signal produced by counter 51 is received and converted by digital-to-analog converter 53 to an analog signal whose voltage is proportional to the number of fatigue cycles experienced by specimen 11. Thus, the signal produced by cycle counter 45, which is the signal produced by digital-to-analog converter 53, is a signal whose voltage increases in discrete steps or levels as the number of fatigue cycles experienced by specimen 11 increases. The signal produced by cycle counter 45 is provided to the horizontal deflection input of oscilloscope 27, to control the abscissa of the dot resulting from detection by transducer 15 of an acoustic emission.

During a fatigue test, each acoustic emission detected by transducer 15 is represented on screen 29 of oscilloscope 27 by a dot located within a two-dimensional cartesian coordinate system. The ordinate of the dot corresponds to the load on the specimen or sample 11 at which the acoustic emission occurred, while the abscissa of the dot corresponds to the number of elapsed fatigue cycles (cycles of cyclic loading) experienced by specimen 11 when the event occurred. Using a storage oscilloscope for oscilloscope 27 to record all dots from acoustic emissions occurring during a test, the positioning of the dots in the resulting display on screen 29 of oscilloscope 27 shows the distribution of acoustic emissions as a function of load and elapsed fatigue cycles.

FIG. 2 shows a display on screen 29 resulting from monitoring, by the device of FIG. 1, of fatigue testing of a Monel 400 IT size compact specimen containing a blunt, work-hardened fatigue crack, over 100,000 cycles of cyclic loading between 1000 lbs. and 4,000 lbs. at 30 Hz. FIG. 2 shows a number of vertical streaks which appear to be uncorrelated with load and which disappear as the test progresses. These are interpreted as being caused by noise from drive mechanism 13. This noise is greatest when the test begins because the connection between specimen 11 and drive mechanism 13 and between specimen 11 and load cell 31 is settling into place on specimen 11, and drive mechanism 13 is reacting to this settling to maintain the minimum 1000 lbs. load on specimen 11. After about 10,000 cycles, the noise from this source is greatly reduced, and continues to decrease with noise activity being largely confined to the lower load ranges. At about 35,000 cycles, the first indication of fatigue cracking appears at maximum load; as the test progresses, this activity causes a distinct line of dots of increasing size to form on screen 29. Thus, the display of FIG. 2 shows the relationship between sample load, acoustic-emission rate, and number of elapsed fatigue cycles. Roughly 100,000 cycles after the first emission indicating fatigue cracking, the presence of the fatigue crack is confirmed visually.

FIG. 3 shows a display on screen 29 resulting from monitoring, by the device of FIG. 1, of fatigue testing of a 300M steel specimen, 1 inch square by ten inches long having a 45°, 0.150 inch deep V-notch in the center and containing a sharp fatigue crack, under three-point bending with loading between zero and 2000 lbs. at 0.25 Hz frequency. For this test, drive mechanism 13 includes two supports for specimen 11, which is positioned horizontally, and a mechanical ram for flexing specimen 11 at its middle. During this testing, the specimen is supported from beneath by two supports, one near each of its two ends, and a mechanical ram flexes the specimen by alternately pressing down on the specimen at its middle and releasing. While the ram presses down on the specimen, the specimen experiences rising load. When the ram retracts to its prerising load position, the specimen experiences falling load. Screen splitter 35 is used during monitoring of this test to split oscilloscope screen 29 horizontally into two displays, the upper display containing rising-load data, and the lower display containing falling-load data. For this test, load cell 31 is mechanically connected to the ram, since specimen 11 is being subjected to flexing loading. The line of dots at 1800 lbs. rising load is attributed to the growth of the fatigue crack. The line of dots at 1500 lbs. falling load is attributed to closure of the fatigue crack. The broad band of activity appearing in FIG. 3 from zero pounds rising load to 300 pounds rising load represents drive mechanism 13 noise caused by the ram striking specimen 11 during crossover between falling load and rising load. When the ram retracts to its prerising load position, the ram lifts off of the surface of specimen 11, so that when rising load is re-initiated, the ram strikes the surface of the specimen, causing noise. This noise is detected by transducer 15 and appears as dots on screen 29. Thus, it is possible with the present invention to distinguish between fatigue-crack propagation, fatigue-crack closure and testing machine noise using a single transducer, and to show the relationship between sample load, acoustic-emission rate, and number of elapsed fatigue cycles.

When several individual acoustic emissions which are detected by transducer 15 during the same fatigue cycle occur at or very near the same load and are positioned on screen 29 very close together, a relatively large, round dot appears on the screen as the result of combination of the dots from the various individual emissions. When such individual emissions occur at somewhat more separated loads but are still sufficiently close together to combine to form a single larger dot, a vertically elongated dot results on screen 29. Thus, both the size and number of dots appearing on screen 29 indicate the number of acoustic emissions detected. Many of the dots shown in FIGS. 2 and 3 result from detection during the same fatigue cycle of more than one acoustic emission by transducer 15 at or very near the same load. For example, there is shown in FIG. 4 a greatly magnified view of dot A of FIG. 3, occurring just before 13,700 fatigue cycles and at about 1200 pounds rising load. As shown in FIG. 4, elongated dot A is composed of several individual dots, each resulting from a separate acoustic emission, and occurring during the same fatigue cycle and at very near the same load.

In summary, operation of the foregoing invention is as follows. Specimen 11 is subjected to cyclic loading by drive mechanism 13, which loading is sensed by load cell 31. Once an acoustic emission event produced by specimen 11 under cyclic loading is detected by transducer 15, the resulting signal from transducer 15 is amplified, filtered and provided to the input of comparator 23. When the amplitude of this signal exceeds the reference voltage which is also provided to comparator 23, indicating that an acoustic emission has occurred, comparator 23 triggers pulse shaper 25 which provides a shaped pulse to the intensity modulation input of oscilloscope 27, causing a dot of light to appear on oscilloscope screen 29. The positioning of this dot on screen 29 is determined as follows. The signal from load cell 31, indicative of instantaneous load on specimen 11, is, depending on the position of double-throw switch 33, either provided directly to the vertical deflection input of oscilloscope 27 to determine the ordinate of the dot on screen 29, or else is provided to screen splitter 35 where it is added to a square wave of proper amplitude and frequency, in phase with and having the same frequency as that of the cyclic loading which specimen 11 experiences, and then provided to the vertical deflection input of oscilloscope 27 to determine the ordinate of the dot on screen 29. In the latter situation, when screen splitter 35 is used, screen 29 is split horizontally into two displays, the upper display containing rising-load data and the lower display containing falling-load data concerning acoustic emissions. The output from load cell 31 is also applied to the input of comparator 47 in series with counter 51 and digital-to-analog converter 53 to derive an analog output signal proportional to the number of elapsed fatigue cycles; this analog signal is used to drive the horizontal deflection input of oscilloscope 27 to determine the abscissa of the dot on screen 29. The display of dots appearing on screen 29 shows the relationship between instantaneous load on specimen 11, acoustic emission rate and number of fatigue cycles.

The device of FIG. 1 can be used for effective monitoring of specimen 11 under spectrum loading, i.e. the application of cyclic loading with varying amplitudes, since it accomplishes the separation of acoustic emission events occurring at different load levels. Thus, the present invention can display fatigue crack growth at less than maximum load during spectrum loading of specimen 11, and enables correlation of emission bursts with load peaks in the block. The interval in which a series of fatigue cycles of varying amplitudes, to be repeated in sequence, is gone through constitutes one fatigue block. For a more compressed display of spectrum loading which is easier to interpret, potentiometer 49 is set so that cycle counter 45 counts only the maximum load in the fatigue block sequence. To accomplish this, potentiometer 49, which determines the reference voltage received by comparator 47, is adjusted so that comparator 47 produces a positive voltage signal only upon sensing the fatigue cycle having the largest maximum amplitude. As a result, fatigue blocks, as opposed to fatigue cycles, appear on the X-axis of the cartesian coordinate system of oscilloscope screen 29.

It should be understood that the foregoing invention can be used with any electromechanical or other materials testing machine capable of applying cyclic load to a specimen. If such a machine has a relay for reversing the loading on the specimen, such that the load on the specimen is rising or falling depending on the position of the relay, then in lieu of screen splitter 35, a double-throw relay whose position is controlled by the position of the testing machine relay can be placed in series with load cell 31 and the vertical deflection input of oscilloscope 27 to place in series or bypass, depending upon its position, a direct current constant voltage source, so that a constant voltage is added to the signal from load cell 31 provided to the vertical deflection input of oscilloscope 27 when the specimen experiences either rising or falling load, as desired, thus horizontally splitting the display on oscilloscope screen 29. In addition, as desired, either the rising load data or the falling load data can be placed in the upper portion of a split oscilloscope display. In screen splitter 35, disclosed above, falling load data can be placed in the upper portion of oscilloscope screen 29 by placing an inverter on the output of either differentiator 37 or amplifier 41. An amplifier can be placed on the output of load cell 31 to provide a stronger signal to screen splitter 35, cycle counter 45 and oscilloscope 27. Amplifiers can also be placed on any or all of the three inputs to oscilloscope 27 to adjust the position and intensity of the display on screen 29 as desired. In addition, in order to produce the display in the present invention, a storage or high-persistence oscilloscope can be used as oscilloscope 27, or a time-exposure camera can be mounted on screen 29 to permanently record on film a time exposure showing all dots appearing on screen 29. A different transducer of different resonance frequency, and a different filter of different bandpass, other than those disclosed above, can be used in the present invention. Furthermore, the various reference voltage inputs for comparators, pulse durations and amplifications disclosed above can be varied as needed. It should also be understood that any load sensing device, such as a piezoelectric or other pressure transducer, capable of producing an electrical signal whose value is proportional to the instantaneous load on the specimen can be used in lieu of the load cell.

Thus there has been provided a novel acoustic emission fatigue analyzer which facilitates the interpretation of dynamic failure processes in materials and the detection of incipient fatigue damage in materials or structures. This acoustic emission fatigue analyzer monitors and receives acoustic emissions from a specimen, produces acoustic emission data which is related more directly to the actual cause of the emissions, detects and displays acoustic emission occurrences and features which would not be observed with conventional acoustic emission monitoring, and is capable of providing data for testing of different crack propagation theories which describe at what part of a loading cycle cracks will propagate. The acoustic emission fatigue analyzer is capable of separating the desired signal from background noise such as is caused by the drive mechanism, thereby providing clearer indication of crack growth. Also, the acoustic emission fatigue analyzer produces a display showing the relationship between instantaneous load on the specimen, acoustic emission rate, and number of elapsed fatigue cycles. Using the invention, it is possible to associate acoustic emission activity with three distinct acoustic emission generators: fatigue crack closure, fatigue crack propagation and the loading mechanism contacting the specimen. The variable threshold of the cycle counter enables the acoustic emission fatigue analyzer to be used with any loading level desired, and is valuable in spectrum loading experiments. Furthermore, in spectrum loading experiments, i.e. experiments in which the maximum load within a cycle is varied, the analyzer allows effective monitoring of specimens, separation of events occurring during different load amplitudes, and correlation of emission bursts with load peaks in the spectrum.

Obviously, many modifications and variations of the present invention are possible in light of the above teachings. It is therefore to be understood that within the scope of the appended claims the invention may be practiced otherwise than as specifically described.

What is claimed is:

1. Apparatus for facilitating analysis of fatiguing of a specimen under cyclic stress, comprising:
triggering means formed to receive acoustic emissions from the specimen for producing a trigger signal upon detection of each of the acoustic emissions;

first deflection means formed to be coupled to the specimen for producing a first deflection signal indicating instantaneous load on the specimen;

second deflection means formed to receive the first deflection signal for producing a second deflection signal indicating the number of elapsed cycles of cyclic stress experienced by the specimen; and recording means connected to receive the trigger, first deflection and second deflection signals for plotting on a plane, upon receiving the trigger signal, a point whose coordinates are determined by the first and second deflection signals.

2. Apparatus as defined in claim 1, furhter comprising: driving means for subjecting a specimen to cyclic stress.

3. Apparatus as defined in claim 1 wherein said recording means comprises an oscilloscope.

4. Apparatus as defined in claim 1 wherein said first deflection means comprises load sensing means for producing an instantaneous load signal.

5. Apparatus as defined in claim 4 wherein said load sensing means comprises a load cell.

6. Apparatus as defined in claim 1, further comprising:

screen splitting means operatively interposed between said first deflection means and said recording means for causing said recording means to make two separate plots on the plane, one plot containing data for emissions produced by the specimen under rising loads and the other plot containing data for emissions produced by the specimen under falling loads; and selecting means operatively interposed between said first deflecting means, said screen splitting means and said recording means for enabling bypass of said screen splitting means.

7. Apparatus as defined in claim 6 wherein said screen splitting means comprises:

differentiating means connected to receive the first deflection signal for producing a differentiated instantaneous load signal;

comparing means connected to receive the load signal for producing a constant voltage signal while said load signal exceeds zero volts;

amplifying means connected to receive the constant voltage signal for producing an amplified constant voltage signal; and summing means connected to receive the first deflection signal and the amplified constant voltage signal for providing a screen splitting deflection signal to said recording means in lieu of the first deflection signal.

8. Apparatus as defined in claim 6 wherein said selecting means comprises a double-throw switch.

9. Apparatus as defined in claim 1 wherein said second deflection means comprises:

comparing means formed to receive the first deflection signal and a reference voltage signal for producing a constant voltage signal while the amplitude of the first deflection signal exceeds the amplitude of the reference voltage signal; and counting means connected to receive the constant voltage signal for producing the second deflection signal.

10. Apparatus as defined in claim 9 wherein said counting means comprises:

a digital counter connected to receive the constant voltage signal for producing a digital count signal indicating the number of times that the constant voltage signal is produced; and a digital to analog converter connected to receive the digital count signal for producing the second deflection signal.

11. Apparatus as defined in claim 9 wherein said second deflecting means further comprises variable threshold means coupled to said comparing means for varying the amplitude of the reference voltage signal.

12. Apparatus as defined in claim 11 wherein said variable threshold means comprises a potentiometer.

13. Apparatus as defined in claim 1 wherein said triggering means comprises:

a transducer formed to be coupled to the specimen for producing a detection signal upon detection of each of the acoustic emissions;

comparing means connected to receive the detection signal and a reference voltage signal for producing a constant voltage signal while the amplitude of the detection signal exceeds the amplitude of the reference voltage signal; and pulse generating means connected to receive the constant voltage signal for producing the trigger signal each time that the constant voltage signal is received.

14. Apparatus as defined in claim 13, further comprising amplifying means operatively interposed between said transducer and said comparing means for amplifying the detection signal.

15. Apparatus as defined in claim 13 wherein said triggering means further comprises filter means operatively interposed between said transducer and said comparing means for removing predetermined frequencies from the detection signal.

16. Apparatus as defined in claim 15 wherein said filter means comprises a bandpass filter.

17. Apparatus as defined in claim 15, further comprising amplifying means operatively interposed between said transducer and said filter for amplifying the detection signal.

18. Apparatus as defined in claim 15, further comprising amplifying means operatively interposed between said filter and said comparing means for amplifying the signal produced by said filter.

* * * * *